United States Patent [19]

Moos

[11] Patent Number: 4,960,815
[45] Date of Patent: Oct. 2, 1990

[54] ISOTOPICALLY-LABELED POLYCYCLIC AMINE DERIVATIVES

[75] Inventor: Walter H. Moos, Ann Arbor, Mich.

[73] Assignee: Warner-Lambert Company, Morris Plains, N.J.

[21] Appl. No.: 465,535

[22] Filed: Jan. 17, 1990

Related U.S. Application Data

[63] Continuation of Ser. No. 247,978, Sep. 22, 1988, abandoned.

[51] Int. Cl.$^5$ .................... A61K 49/02; C07C 211/00
[52] U.S. Cl. ...................................... 424/1.1; 564/308
[58] Field of Search .......................... 424/1.1; 564/308

[56] References Cited

U.S. PATENT DOCUMENTS 3,111,527  11/1963  Godefroi .............................. 260/576
3,159,677  12/1964  Godefroi .............................. 260/576

OTHER PUBLICATIONS

Drug Development for Senile Cognitive Decline, J. Med. Chem., 1986, 29, 1125, Hershenson, et al.
Chapter 4, Cognitive Disorders, Annual Reports in Medicinal Chemistry-21, 1986, Hershenson, et al.
Developmental Neuropsychology, 1986 2(4), 261-276.
Neuroscience Letters, 74 (1987) 371-376.
European Journal of Pharmacology, 123 (1986) 173-174.
Science, vol. 227, Alteratins in 1-Glutamate Binding in Alzheimer's and Huntington's Diseases.
Godefroi et al "t-Carbinamines Derived from Pardaur Hydrogenated Fluorenes and Dibenzofucanes", J. Org. Chem. vol. 28, (1967), pp. 1112-1119.
Godero et al., "t-Carbinamines Derived from Partially Hydrogenated Fluorenes and Dibenzofuranes," J. Org. Chem., vol. 28, (1963), pp. 1112-1119.

Primary Examiner—John S. Maples
Attorney, Agent, or Firm—Elizabeth M. Anderson

[57] ABSTRACT

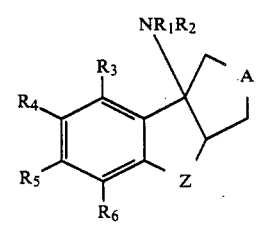

A series of isotopically-labeled fluorenamine, dibenzofuranamine, and dibenzothiophenamine derivatives useful for diagnosing neurodegenerative disorders in mammals wherein a detectable amount of an isotape-labeled fluorenamine, dibenzofuranamine, or dibenzothiophenamine derivative is used.

4 Claims, No Drawings

ISOTOPICALLY-LABELED POLYCYCLIC AMINE DERIVATIVES

This application is a continuation of Ser. No. 247,978, filed Sept. 22, 1988, now abandoned.

BACKGROUND OF THE INVENTION

The present invention covers a series of isotopically-labeled fluorenamine, dibenzofuranamine, and dibenzothiophenamine derivatives useful in the diagnosis of neurodegenerative disorders.

U.S. Pat. No. 3,159,677, 3,206,480 and 3,111,527 cover unlabeled fluorenamines, dibenzofuranamines, dibenzothiophenamines and processes for preparing them. The compounds are disclosed as having useful central nervous system depressant activity.

In *Science*, 227, 1496-1499 (1985), alterations in L-glutamate binding have been observed in Alzheimer's disease (AD; including primary degenerative dementia (PDD), senile dementia of the Alzheimer type (SDAT), and chronic organic brain syndrome (OBS)) and Huntington's (HD) disease, amongst other neurodegenerative disorders. Additional candidate disorders include, for example, Age-Associated Memory Impairment (AAMI; *Dev Neuropsychol*, 2, 261-276 (1986); including benign senescent forgetfulness (BSF) and mild-memory impairment (MMI)), and the constellation of disorders that can be described as Senile Cognitive Decline (SCD; *J Med Chem*, 29, 1125-1130 (1986); *Annu Rep Med Chem*, 21, 31-40 (1986); *Med Res Rev*, 8, 353-391 (1988)).

Glutamate is the putative neurotransmitter of both intracortical association fibers and cortical efferents to many subcortical structures, including caudate and putamen. Because glutamate and some of its analogues are neurotoxic, it has been proposed that abnormalities in glutamate neurotransmitter function may play a causative role in neurodegenerative disorders such as HD and olivopontocerebellar atrophy. Furthermore, a high correlation has been observed between the localization of 1-[1-(2-thienyl)cyclohexyl]piperidine (TCP), an analogue of phencyclidine (PCP), binding sites and N-methyl-D-aspartate (NMDA), a glutamate analogue, receptors in *Eur J Pharmacol*, 123, 173-174 (1986). Finally, a loss of hippocampal TCP binding in AD has been reported in *Neurosci Lett*, 74, 371-376 (1987).

TABLE 1
Some Stable and Radioactive Isotopes

| Isotope | Relative natural abundance | Decay mode (type of radiation) | Half-life | Maximum specific activity (Ci/mol) |
|---|---|---|---|---|
| $^2$H | 0.0154 | stable | | |
| $^3$H | | β− | 12.35 years | $2.90 \times 10^4$ |
| $^{11}$C | | β+ | 20.3 minutes | $9.22 \times 10^9$ |
| $^{13}$C | 1.1 | stable | | |
| $^{14}$C | | β− | 5,730 years | 62.4 |
| $^{13}$N | | β+ | 9.96 minutes | $1.89 \times 10^{10}$ |
| $^{15}$N | 0.365 | stable | | |
| $^{15}$O | | β+ | 2 minutes | $9.25 \times 10^{10}$ |
| $^{18}$O | 0.204 | stable | | |
| $^{18}$F | | β+ | 109.7 minutes | $1.71 \times 10^9$ |
| $^{35}$S | | β− | 87.1 days | $1.5 \times 10^6$ |
| $^{36}$Cl | | β− | $3.1 \times 10^5$ years | |
| $^{122}$I | | gamma | 3.6 minutes | |
| $^{123}$I | | gamma | 13.3 hours | |
| $^{131}$I | | β−, gamma | 8 days | |

As shown in Table 1 above a variety of stable- and radio-active isotopes are of interest in the instant invention. Certain isotope terminologies are equivalent, and are used herein interchangeably, for example, $^2$H=H-2=D=deuterium; $^3$H=H-3=T=tritium. Further information on isotopes can be found in *The Merck Index,* Tenth Edition (Merck; Rahway, New Jersey: 1983), edited by M. Windholz et al.

Additional background information can be found in *Synthesis and Applications of Isotopically Labeled Compounds*, Proceedings of an International Symposium, Kansas City, MO, June 6-11, 1982 (Elsevier; Amsterdam, Netherlands: 1983), edited by W. P. Duncan and A. B. Susan.

SUMMARY

The present invention covers isotopically-labeled compounds of formula 1

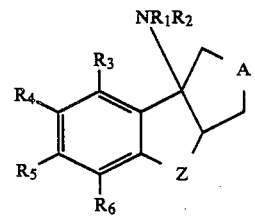

wherein $R_1$–$R_6$, Z, and A are as defined below:

Preferred compounds of the present invention are those wherein:

$R_1$ is hydrogen, methyl, ethyl, or trifluoropropyl;

$R_3$, $R_4$, $R_5$, and $R_6$ are each hydrogen, or $R_4$ and $R_5$ are taken together and are methylenedioxy;

Z is methylene;

A is —CH$_2$CH$_2$— or —HC=CH—;

wherein at least one hydrogen, carbon, nitrogen, fluorine, chlorine, bromine, or iodine is replaced by a stable- or radio-isotope $^2$H, $^3$H*, $^{11}$C*, $^{13}$C, $^{14}$C*, $^{13}$N*, $^{15}$N, $^{18}$F*, $^{34m}$Cl, $^{36}$Cl*, $^{74}$Br*, $^{75}$Br*, $^{76}$Br*, $^{77}$Br*, $^{82}$Br*, $^{122}$I*, $^{123}$I*, $^{125}$I*, or $^{131}$I*, respectively.

More preferred compounds of the present invention are those wherein at least on hydrogen, carbon, or nitrogen is replaced by a radio-isotope including $^3$H*, $^{11}$C*, $^{14}$C*, or $^{18}$F*

Especially preferred radioisotopically-labeled compounds of the instant invention are:

1,2,3,4,9,9a-hexahydro-(N-ethyl-(2-$^{11}$C))-4aH-fluoren-4a-amine, (7-fluoro-$^{18}$F)-1,2,3,4,9,9a-hexahydro-N-methyl-4aH-fluoren-4a-amine, (7-fluoro-$^{18}$F)-1,3,4,9a-tetrahydro-N-methyl-fluoren-4a(2H)-amine, 6,7,8,9-tetrahydro-(N-methyl-$^{14}$C)-9a(5aH)-dibenzothiophenamine, 6,7,8,9-tetrahydro-N-methyl-9a(5aH)-dibenzothiophen(7,8-t$_2$)-amine, 6,7,8,9-tetrahydro-(N-methyl-$^{14}$C)-9a(5aH)-dibenzothiophen(7,8-t$_2$)-amine, 6,7,8,9-tetrahydro-(N-ethyl-(2-$^{11}$C))-9a(5aH)-dibenzothiophenamine, 7-fluoro-$^{18}$F)-6,7,8,9-tetrahydro-N-methyl-9a(5aH)-dibenzothiophenamine, 6,7,8,9-tetrahydro-(N-(3,3,3-trifluoropropyl-$^{18}$F$_3$)) -9a(-5aH)-dibenzothiophenamine;

6,9-dihydro-(N-methyl-$^{14}$C)-9a(5aH)-dibenzothiophenamine, 6,9-dihydro-N-methyl-9a(5aH)-dibenzothiophen-(7,8-t₂)amine,
6,9-dihydro-(N-methyl-¹⁴C)-9a(5aH)-dibenzothiophen(7,8-t₂)-amine and 6,9-dihydro-(N-ethyl-(2-¹¹C))-9a(5aH)dibenzothiophenamine.

Most especially preferred compounds are:
1,2,3,4,9,9a-hexahydro-(N-methyl-¹¹C)-4aH-fluoren-4a-amine,
1,4,9,9a-tetrahydro-(N-methyl-¹¹C)-4aH-fluoren-4a-amine,
1,2,3,4,9,9a-hexahydro-(N-methyl-¹⁴C)-4aH-fluoren-4a-amine,
1,4,9,9a-tetrahydro-(N-ethyl-(2-¹¹C))-4aH-fluoren-4a-amine,
1,4,9,9a-tetrahydro-(N-(3,3,3-trifluoropropyl-¹⁸F₃))-4aH-fluoren-4a-amine,
6,7,8,9-tetrahydro-(N-methyl-¹¹C)-9a(5aH)-dibenzothiophenamine,
6,9-dihydro-(N-methyl-¹¹C)-9a(5aH)-dibenzothiophenamine,
6,7,8,9-tetrahydro-(N-methyl-¹¹C)-9a(5aH)-dibenzofuranamine,
6,9-dihydro-(N-methyl-¹¹C)-9a(5aH)-dibenzofuranamine.

Preferred stable isotope-labeled compounds are:
1,2,3,4,9,9a-hexahydro-N-methyl-4aH-fluoren-(2,3-d₂)4a-amine,
1,2,3,4,9,9a-hexahydro-(N-methyl-¹³C)-4aH-fluoren(2,3-d₂)-4a-amine,
6,7,8,9-tetrahydro-(N-methyl-¹³C)-9a(5aH)-dibenzothiophenamine,
6,7,8,9-tetrahydro-N-methyl-9a(5aH)-dibenzothiophen(7,8-d₂)-amine,
6,7,8,9-tetrahydro-(N-methyl-¹³C)-9a(5aH)-dibenzothiophen-(7,8-d₂)-amine,
6,9-dihydro-(N-methyl-¹³C)-9a(5aH)-dibenzothiophenamine,
6,9-dihydro-N-methyl-9a(5aH)-dibenzothiophen-(7,8-d₂)amine,
6,9-dihydro-(N-methyl-¹³C)-9a(5aH)-dibenzothiophen(7,8-d₂)-amine,
6,7,8,9-tetrahydro-(N-methyl-¹³C)-9a(5aH)-dibenzofuranamine,
6,7,8,9-tetrahydro-N-methyl-9a(5aH)-dibenzofuran(7,8-d₂)-amine,
6,7,8,9-tetrahydro-(N-methyl-¹³C)-9a(5aH)-dibenzofuran-(7,8-d₂)-amine,
6,9-dihydro-(N-methyl-¹³C)-9a(5aH)-dibenzofuranamine,
6,9-dihydro-N-methyl-9a(5aH)-dibenzofuran-(7,8-d₂)amine, and
6,9-dihydro-(N-methyl-¹³C)-9a(5aH)-dibenzofuran(7,8-d₂)-amine.

The compounds of the present invention are useful in the diagnosis of diseases of the central nervous system. Such disorders include but are not limited to neurodegenerative disorders such as Alzheimer's disease, Age-Associated Memory Impairment, and Huntington's disease.

Also included is a method of administering the compounds.

A preferred method of administration is intravenous.

Processes for preparing the compounds are also included.

A process for the preparation of a compound of formula I which comprises:

(a) hydrogenation of the olefin, that is a tetrahydrofluorenamine or a dihydro-dibenzofuranamine or -dibenzothiophenamine derivative, using deuterium or tritium gas in the presence of a catalyst, or catalytic tritium exchange, thereby providing deuterated or tritiated hexahydrofluorenamine or tetrahydro-dibenzofuranamine or -dibenzothiophenamine derivatives;

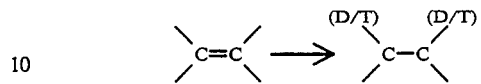

(b) metal hydride reduction, for example with deuterated or tritiated lithium aluminum hydride, as in the reduction of a carbamate to provide an alkyl amine, or an amide to provide an alkyl amine;

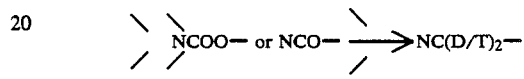

(c) use of labeled reagents in alkylations or acylations, such as, for example, labeled acyl halides like acetyl chloride or labeled anhydrides like acetic anhydride to convert an amine to an amide; labeled alkyl halides like methyl iodide or ethyl iodide or 3,3,3-trifluoropropyl iodide to convert an amine to an alkyl amine or an alkyl amine to a dialkyl amine or a dialkyl amine to a trialkylammonium salt; or labeled aldehydes like formaldehyde to reductively alkylate amines, for example using formic acid as a hydride transfer agent; particularly in the case of [¹¹C*]-labeled reagents;

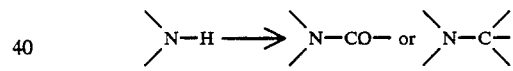

(d) exchange of halides or other good leaving groups (L) like alkyl or aryl sulfonates or oxymercurials or the like with isotopically-labeled halides (Hal);

L-aryl or L-alkyl→Hal-aryl or Hal-alkyl (e) use of labeled amines like substituted or unsubstituted benzyl amines with appropriately substituted cycloalkanones to form intermediate amines followed by metal halogen exchange and a standard workup.

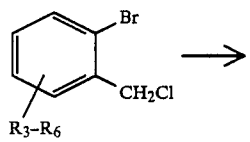

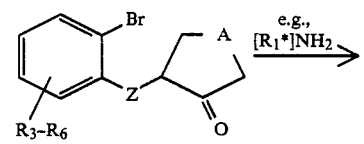

-continued

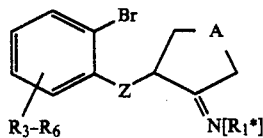

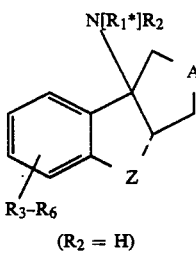

($R_2 = H$)

DETAILED DESCRIPTION

The present invention provides radio- or stable-isotopically-labeled compounds which unexpectedly bind especially to sites labeled by TCP. These compounds, therefore, are useful as tools for the diagnosis of neurodegenerative disorders.

Compounds of the present invention may also be described as ligands for the aforementioned sites, wherein "ligand" refers to an agent that reacts to form a covalent, ionic, association or non-covalent complex with one or more molecules such as a receptor. Hereinafter, "isotopically-labeled" or "isotope-labeled" will be used to describe either radioactive isotopes, hereafter indicated by an asterisk ("*"), or stable (i.e., nonradioactive) low natural abundance isotopes. Singly-, doubly-, and multiply-labeled compounds are all included within the scope of this invention. For example, compounds of the instant invention may simultaneously include both tritium and carbon-14. In particular, the present invention provides appropriately labeled fluorenamine, dibenzofuranamine, and dibenzothiophenamine positron emission tomography (PET) ligands useful in the diagnosis of neurodegenerative disorders in vivo. Other diagnostic methods of the present invention include but are not limited to magnetic resonance imaging (MRI), single photon emission computed tomography (SPECT), and in vitro or ex vivo autoradiographic techniques. Nonlimiting examples useful in these diagnostic methods include stable, or beta ($\beta-$), gamma, or positron ($\beta+$) emitting isotopes such as $^2H$, $^3H^*$, $^{11}C^*$, $^{13}C$, $^{14}C^*$, $^{13}N^*$, $^{15}N$, $^{15}O^*$, $^{18}O$, $^{18}F^*$, $^{35}S^*$, $^{34}Cl^*$, $^{36}Cl^*$, $^{74}Br^*$, $^{75}Br^*$, $^{76}Br^*$, $^{77}Br^*$, $^{82}Br^*$, $^{122}I^*$, $^{123}I^*$, $^{125}I^*$, or $^{131}I^*$.

Isotopic enrichment of $\geq 99\%$ is feasible in many cases for stable isotopes such as, for example, deuterium, carbon-13, or nitrogen-15. Simple short-lived $\beta+$ emitter labeled compounds readily accessible as precursors in the synthesis of radiotracers include, but are not limited to, carbon-11: CO, $CO_2$, HCN, HCHO, MeI, $COCl_2$; fluorine-18: $F_2$, HF (anhydrous or aqueous), MeCOOF, $ClO_3F$; nitrogen-13: $NH_3$, $NO_2-$, $NO_3-$.

The present invention is for an isotopically-labeled compound of formula

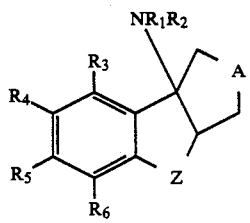

or a pharmaceutically acceptable acid addition salt thereof wherein:

$R_1$ is hydrogen, lower alkyl, lower carboalkoxy, lower alkylcarbonyl, or benzyl wherein the alkyl, carboalkoxy, alkylcarboxyl or benzyl is unsubstituted or substituted by one or more lower alkoxy groups, dialkylamino groups, or halogen atoms;

$R_2$ is hydrogen or lower alkyl;

$R_3$, $R_4$, $R_5$ and $R_6$ are each independently hydrogen, lower alkyl, lower alkoxy, or halogen or $R_3$ and $R_4$, $R_4$ and $R_5$, $R_5$ and $R_6$ when taken together are methylenedioxy;

Z is oxygen, sulfur, sulfur dioxide or methylene; and

A is $-HC=CH-$, $-CMe=CMe-$, $(CH_2)_2$, $(CHMe)_2$, or $CH_2CHMe$, wherein one or more hydrogen, carbon, nitrogen, oxygen, fluorine, sulfur, chlorine, bromine, or iodine is replaced by a stable- or radio-isotope including $^2H$, $^3H^*$, $^{11}C^*$, $^{13}C$, $^{14}C^*$, $^{13}N^*$, $^{15}N$, $^{15}O^*$, $^{18}O$, $^{18}F^*$, $^{35}S^*$, $^{34m}Cl^*$, $^{36}Cl^*$, $^{74}Br^*$, $^{75}Br^*$, $^{76}Br^*$, $^{77}Br^*$, $^{82}Br^*$, $^{122}I^*$, $^{123}I^*$, $^{125}I^*$, or $^{131}I^*$, respectively.

Compounds such as those listed in Table 2 were prepared, for example, using the general routes outlined in Schemes I and II below. Details of the chemistry have appeared in *J Org Chem*, 28, 1112–1119 (1963), and in the aforementioned patents Additional useful synthetic methods can be found, for example, in U.S. Pat. Nos. 4,209,614, 4,243,608, and 4,647,446, and in U.K. patent application No. 2,003,480. Reference is also made to the methods described and cited in *J Med Chem*, 31, 362–366 (1988) and in *Synthesis and Applications of Isotopically Labeled Compounds*, Proceedings of an International Symposium, Kansas City, MO, June 6–11, 1982 (Elsevier; Amsterdam, Netherlands: 1983), edited by W. P. Duncan and A. B. Susan. Further general synthetic methods pertinent to the instant invention can be found, for example, in *Advanced Organic Chemistry*, Third Edition (Wiley; New York, NY: 1985), by J. March, *Vogel's Textbook of Practical Organic Chemistry*, Fourth Edition (Longman; London, England: 1978), by B. S. Furniss et al., or *Modern Synthetic Reactions*, Second Edition (Benjamin; Menlo Park, CA: 1972), by H. O. House.

Synthesis of the compounds in the instant invention is accomplished as follows, using the fluorenamine series as the main illustrative and representative example.

The starting indene (or benzofuran or benzothiophene) carboxylates II (optionally substituted, for example, in the aromatic moiety with alkyl groups such as methyl, alkoxy groups, halogens, or methylenedioxy) are known and readily available, as are the dihalogenated toluenes VII and ortho-halogenated phenols (or thiophenols) XI.

Respectively: Known carbamates or amides IV or VI may be reduced with labeled lithium aluminum hydride to provide secondary amines V or VII. Known secondary amine VII may be hydrogenated using deuterium or tritium gas to provide labeled secondary amine VII. Known primary amines V or VII may be alkylated with labeled alkyl halide or formaldehyde to provide labeled secondary amines V or VII. Known primary amines V or VII may be acylated with labeled anhydride or acyl halide to provide amides V or VII, particularly wherein $R_1$ is acetyl.

Alternatively, compounds of formula V, wherein $R_1$ is benzyl for example, may be prepared by initial metal halogen exchange on the known X, followed by the standard workup.

Scheme I

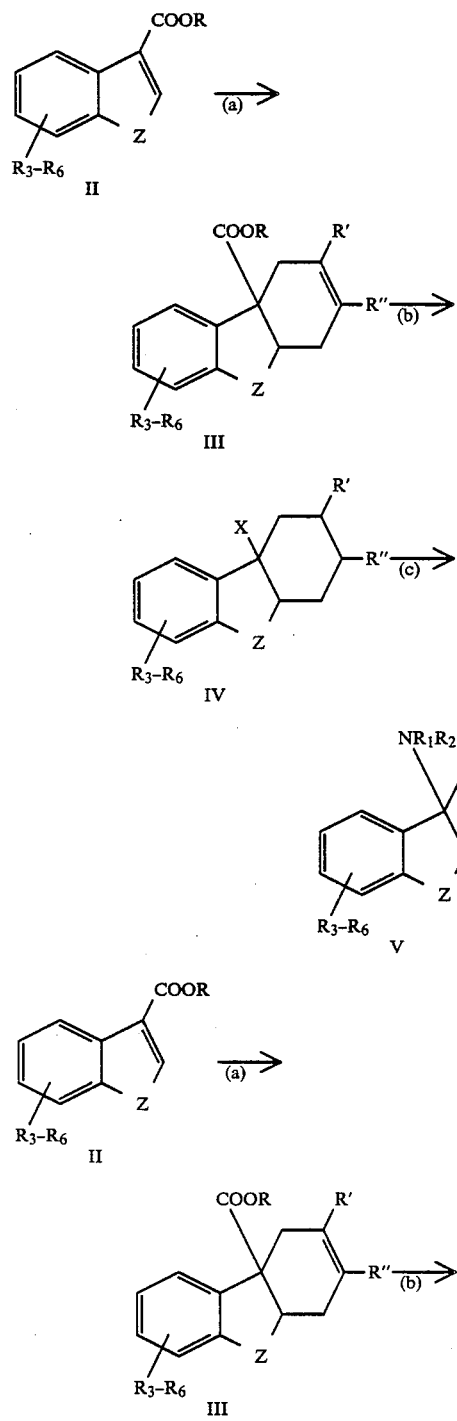

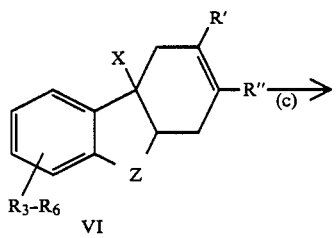

Wherein R is, for example, hydrogen or alkyl; R' and R" are, for example, hydrogen or methyl; X can be COOR or $NR_1N_2$.

Scheme II

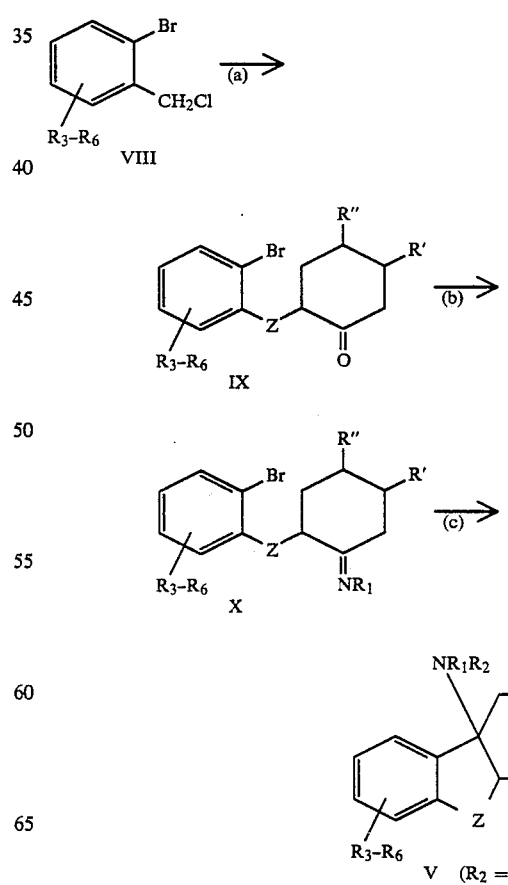

-continued
Scheme II

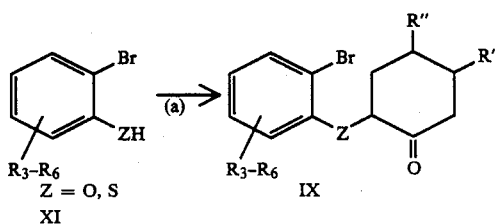

Preparation of isotope-labeled compounds is achieved, for example:

(1) by hydrogenation of the olefin using tritium gas in the presence of a catalyst, thereby providing tritiated material;

(2) by catalytic tritium exchange (see, for example, *J Labeled Compounds Radiopharm,* 21, 575-586 (1984); *Nucleonics,* 20, 98-102 (1962); *J Am Chem Soc,* 79, 1013 (1957));

(3) by metal hydride reduction (e.g., tritiated LiAlH$_4$ reduction of carbamates (—NHCOOR) to provide amines (—NH[Me*]), or amides (—NHCOR) to provide amines (NH[CH$_2$*]R));

(4) through the use of labeled reagents in alkylations or acylations, such as, for example, [CH$_3$*]I in methylations (e.g., NH$_2$→NHMe; NHMe→NMeMe), or [CH$_2$O*] in reductive methylations (e.g., using HCOOH for hydride transfer), particularly in the case of [$^{11}$C*]-labeled reagents and the preparation of [$^{11}$C*]-labeled material;

(5) through exchange of halides with isotopically-labeled halides.

Stable isotopically-labeled compounds are prepared using labeled precursors or by replacing, for example, tritium with deuterium in the aforementioned methods.

The term alkyl, except where otherwise stated, in alkyl per se or in alkoxyalkyl or in alkylcarbonyl, is a straight or branched chain of from one to six carbon atoms.

The term alkoxyalkyl is selected from among alkoxy radicals containing not more than six carbon atoms and includes methoxy, ethoxy, propyloxy, and the like.

The term halogen means fluorine, chlorine, bromine, and iodine. The preferred halogen is fluorine.

The term isotope includes but is not limited to $^2$H, $^3$H*, $^{11}$C*, $^{13}$C, $^{14}$C*, $^{13}$N*, $^{15}$N, $^{15}$O*, $^{18}$O, $^{18}$F*, $^{35}$S*, $^{34m}$Cl*, $^{36}$Cl*, $^{74}$Br*, $^{75}$Br*, $^{76}$Br*, $^{77}$Br*, $^{82}$Br*, $^{122}$I*, $^{123}$I*, $^{125}$I*, or $^{131}$I*.

The term lower carboalkoxy is selected from among alkoxycarbonyl moieties containing not more than six carbon atoms.

Preferred lower carboalkoxy groups are, for example, carbomethoxy and carboethoxy.

The term lower alkylcarbonyl denotes substituent alkyl groups as previously defined attached to the parent molecular moiety through a carbonyl group.

Preferred lower alkylcarbonyl groups are, for example, acetyl and propionyl.

The benzyl may be unsubstituted or substituted by alkyl, alkoxy or halogen.

Preferred substituents are methyl, methoxy and fluorine.

Possible amino substituents include but are not limited to methyl, ethyl, 3,3,3-trifluoropropyl, acetyl, and carbomethoxy.

Possible di-alkylamino groups include but are not limited to dimethyl and diethyl.

TABLE 2

| $R_1$ | $R_2$ | $R_3$ | $R_4$ | $R_5$ | $R_6$ | Z | A | Comments |
|---|---|---|---|---|---|---|---|---|
| Some Preferred Compounds Appropriately Isotope-Labeled | | | | | | | | |
| H | H | H | H | H | H | CH$_2$ | CH$_2$CH$_2$ | |
| Me | H | H | H | H | H | CH$_2$ | CH$_2$CH$_2$ | e.g., A = CHTCHT, A = CHDCHD, $R_1$ = $^{11}$CH$_3$, $^{13}$CH$_3$, or $^{14}$CH$_3$ |
| Me | Me | H | H | H | H | CH$_2$ | CH$_2$CH$_2$ | e.g., A = CHTCHT, A = CHDCHD, $R_1$ = $^{11}$CH$_3$, $^{13}$CH$_3$, or $^{14}$CH$_3$ |
| Et | H | H | H | H | H | CH$_2$ | CH$_2$CH$_2$ | eg., A = CHTCHT or $R_1$ = $^{13}$CH$_3$CD$_2$ |
| nPr | H | H | H | H | H | CH$_2$ | CH$_2$CH$_2$ | |
| COOMe | H | H | H | H | H | CH$_2$ | CH$_2$CH$_2$ | |
| (CH$_2$)$_4$Me | H | H | H | H | H | CH$_2$ | CH$_2$CH$_2$ | |
| CH$_2$CH$_2$NEt$_2$ | H | H | H | H | H | CH$_2$ | CH$_2$CH$_2$ | |
| CH$_2$CH(OEt)$_2$ | H | H | H | H | H | CH$_2$ | CH$_2$CH$_2$ | |
| (CH$_2$)$_3$OMe | H | H | H | H | H | CH$_2$ | CH$_2$CH$_2$ | |
| Me | H | H | —OCH$_2$O— | | H | CH$_2$ | CH$_2$CH$_2$ | |
| Et | H | H | —OCH$_2$O— | | H | CH$_2$ | CH$_2$CH$_2$ | |
| (CH$_2$)$_3$OMe | H | H | —OCH$_2$O— | | H | CH$_2$ | CH$_2$CH$_2$ | |
| Me | H | OMe | OMe | OMe | H | CH$_2$ | CH$_2$CH$_2$ | |
| Me | H | H | H | H | H | CH$_2$ | CH(Me)CH$_2$ | |
| Me | H | H | H | H | H | CH$_2$ | CHMeCHMe | |
| nPr | H | H | H | H | H | CH$_2$ | CHMeCHMe | |
| H | H | H | H | H | H | CH$_2$ | CH=CH | |
| Me | H | H | H | H | H | CH$_2$ | CH=CH | e.g., A = CHTCHT, A 32 CHDCHD, $R_1$ = $^{11}$CH$_3$, $^{13}$CH$_3$, or $^{14}$CH$_3$ |
| The More Preferred Compounds (appropriately Isotope-Labeled) | | | | | | | | |
| Me | Me | H | H | H | H | CH$_2$ | CH=CH | |
| Et | H | H | H | H | H | CH$_2$ | CH=CH | |
| nPr | H | H | H | H | H | CH$_2$ | CH=CH | |

TABLE 2-continued

| $R_1$ | $R_2$ | $R_3$ | $R_4$ | $R_5$ | $R_6$ | Z | A | Comments |
|---|---|---|---|---|---|---|---|---|
| COOMe | H | H | H | H | H | $CH_2$ | CH=CH | |
| H | H | H | H | H | H | $CH_2$ | CMe=CMe | |
| Me | H | H | H | H | H | $CH_2$ | CMe=CMe | |
| Me | Me | H | H | H | H | $CH_2$ | CMe=CMe | |
| Et | H | H | H | H | H | $CH_2$ | CMe=CMe | |
| nPr | H | H | H | H | H | $CH_2$ | CMe=CMe | |
| Me | H | H | H | H | H | O | $CH_2CH_2$ | |
| Me | Et | H | H | H | H | O | $CH_2CH_2$ | e.g., $R_2 = CH_3CD_2$ or $CH_3CT_2$ |
| Et | H | H | H | H | H | O | $CH_2CH_2$ | |
| nPr | H | H | H | H | H | O | $CH_2CH_2$ | |
| $(CH_2)_2NEt_2$ | H | H | H | H | H | O | $CH_2CH_2$ | |
| $CH_2CH(OEt)_2$ | H | H | H | H | H | O | $CH_2CH_2$ | |
| $(CH_2)_3OM3$ | H | H | H | H | H | O | $CH_2CH_2$ | |
| Me | H | H | H | H | H | S | $CH_2CH_2$ | |
| Me | Et | H | H | H | H | S | $CH_2CH_2$ | |
| Me | H | H | H | H | H | S | CH=CH | |
| Me | Me | H | H | H | H | S | CH=CH | |
| Me | Et | H | H | H | H | S | CH=CH | |
| Me | H | H | H | H | H | $SO_2$ | $CH_2CH_2$ | |
| COOMe | H | H | H | H | H | $SO_2$ | $CH_2CH_2$ | |
| COOMe | H | H | H | H | H | $SO_2$ | CH=CH | |
| $CH_2CH_2CF_3$ | H | H | H | H | H | $CH_2$ | $CH_2CH_2$ | e.g., $R_1 = CH_2CH_2C^{18}F_3$ |

Preferred exemplary locations for the labels in Table 2 are in R1, R2, and/or A, particularly as follows. R1 and/or R2, each independently: H-2 or H-3 in $C[H_3*]$ or $C[H_2*]CH_3$; C-11, C-12, C-13, or C-14 in $C[*]H_3$, $C[*]H_2CH_3$, $CH_2C[*]H_3$; F-18 in the 3,3,3-trifluoropropyl substituent; doubly labeled as in $^{14}C^3H_3$; triply labeled as in $^{13}C^2H_2CH_2C^{18}F_3$. A: —DHC—CHD—; —THC—CHT—.

Compounds of the instant invention include solvates, hydrates, and salts of the compounds of formula I above.

A compound of formula I above is useful both in the free base form and in the form of acid addition salts and both forms are within the scope of the invention. The term pharmaceutically acceptable acid addition salt is intended to mean relatively nontoxic acid addition salts from either inorganic or organic acids such as, for example, hydrochloric, hydrobromic, sulfuric, phosphoric, citric, oxalic, malonic, acetic, maleic, salicylic, ethanesulfonic, malic, gluconic, fumaric, succinic, ascorbic, methanesulfonic, benzenesulfonic, p-toluenesulfonic, and the like as would occur to one skilled in the art.

The acid addition salts of the basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

In applications of this invention, the compounds can be used either as free bases or in the form of acid addition salts. The acid addition salts are preferred where greater water solubility is desired.

The above compounds are useful, for example, as agents for positron or single photon imaging. Once administered, the radioactive compounds reach the brain and provide labeled ligands which may be detectable by positron emission tomography or single photon emission computed tomography, or magnetic resonance.

The compounds used in the invention may contain asymmetric carbon atoms. This invention includes the use of individual enantiomers or diastereomers or mixtures thereof which may be prepared or isolated by methods known in the art.

The compounds of the instant invention are useful in a method for diagnosing central nervous system disorders using in vitro or ex vivo techniques which may comprise analyzing mammalian tissue treated with detectable amount of a compound of formula I using an isotopically-sensitive imaging scanner.

The imaging method employed may be autoradiography, single photon emission computed tomography, or magnetic resonance.

The disorder diagnosed may be neurodegenerative, such as but not limited lo Alzheimer's disease, Huntington's disease, Age-Associated Memory Impairment.

Amounts of a compound used may vary from concentrations of 1 femtogram per milliliter to 100 milligrams per milliliter.

The method may employ, for example, mammalian brain tissue.

The compounds of the instant invention may be administered by any convenient or effective method for introducing foreign substances into the blood stream of mammals. The weight dosage of the labeled compounds does not appear to be critical and the lower weight dosage limit would depend only on the lower detection limits of the imaging device used. The isotope-labeled compounds of the present invention may be diluted by conventional pharmaceutical carriers for administration into the subject. Intravenous injection is a preferred method. Dosage of a detectable level of isotopically-labeled compound is required, and may range from tracer levels at or below 1 femtogram per kilogram, to non-tracer levels of up to 1 gram per kilogram body weight, with compound weight calculated on a free base basis, depending upon the potency of the compound, its receptor kinetics and thermodynamics, and pharmacokinetic and pharmacodynamic factors. An imaging scanner may be a commercially available unit such as, for example, a Positron Emission Transaxial Tomograph, a Single Photon Emission Computerized Tomograph, a conventional scintillation camera, or a Magnetic Resonance Imaging Spectrometer.

Pharmacology

The ability of the compounds of the instant invention to interact with PCP receptors is shown in the following table. Tritiated TCP binding, designated RBS1, was carried out essentially as described in *J Pharmacol Exp Ther*, 238, 739–748 (1986).

TABLE 3
Representative Binding Results

| $R_1$ | $R_2$ | $R_3$ | $R_4$ | $R_5$ | $R_6$ | Z | A | RBS1 $IC_{50}$ |
|---|---|---|---|---|---|---|---|---|
| H | H | H | H | H | H | $CH_2$ | $CH_2CH_2$ | 27 nM |
| Me | H | H | H | H | H | CH | $CH_2CH_2$ | 15 nM |
| $(CH_2)_3OMe$ | H | H | H | H | H | $CH_2$ | $CH_2CH_2$ | 102 nM |
| Me | H | H | H | H | H | $CH_2$ | $CH(Me)CH_2$ | 95 nM |
| Et | H | H | H | H | H | O | $CH_2CH_2$ | 141 nM |
| Me | H | H | H | H | H | S | $CH_2CH_2$ | 10 nM |
| PCP | — | (reference standard) | | | | — | | 40 nM |
| TCP | — | (reference standard) | | | | — | | 9 nM |
| ketamine | — | (reference standard) | | | | — | | 860 nM |
| MK-801 | — | (reference standard) | | | | — | | 3 nM |

The following examples are illustrative. They are not intended to in any way limit the scope of the invention. In general, synthesis of isotope-labeled compounds is accomplished by substituting an isotope-labeled reagent for an unlabeled one using the synthetic paths previously reported for the unlabeled compounds, on small scales.

EXAMPLE 1

N-Methyl-1,2,3,4,9,9a-hexahydro-4aH-fluoren-4a-amine

A. General procedure: A solution of 5 g of N-methyl-1,4,9,9a-tetrahydro-4aH-fluoren-4a-amine hydrochloride in 100 ml of methanol is hydrogenated by shaking it with 0.5 g of 20% palladium on charcoal catalyst in contact with a hydrogen atmosphere. When the theoretical amount of hydrogen corresponding to hydrogenation of one double bond has been absorbed, the catalyst is removed by filtration and the solvent distilled under reduced pressure to yield N-methyl1,2,3,4,9,9a-hexahydro-4aH-fluoren-4a-amine hydrochloride; mp 202° to 203° C. following recrystallization from methanol-ether. The free base is obtained by treating an aqueous solution of the hydrochloride with sodium hydroxide and extracting with ether. The hydrobromide is obtained by adding a slight excess of hydrogen bromide to a solution of the free base in ether.

B. Deuterium-labeled material: Prepared as in A. except in contact with an atmosphere containing deuterium gas.

C. Tritium-labeled material: Prepared as in A. except in contact with an atmosphere containing tritium gas.

EXAMPLE 2

N,N-Dimethyl-1,2,3,4,9,9a-hexahydro-4aH-fluoren-4a-amine

A. General procedure: To 6 9 of N-methyl1,2,3,4,9-,9a-hexahydro-4aH-fluoren-4a-amine is added 3.04 g of 98% formic acid and then 2.56 g of a 37 wt. % solution of formaldehyde in water. The mixture is heated at 90° to 100° C. for five hours and allowed to stand at room temperature for 16 hours. It is then made basic with 5N sodium hydroxide solution and the liberated free base is removed by extraction with several portions of ether. The combined ethereal extract is dried and evaporated and the residue is distilled under high vacuum. The desired amine is obtained as a fraction boiling at about 90° to 96° C. at 0.15 mm Hg. The hydrochloride is prepared by treating an ethereal solution of the free base with a slight excess of hydrogen chloride in isopropyl alcohol. After crystallizing the product from a mixture of dioxane and ether, it melts at about 158° to 160° C. When methanolic solutions of the free base and maleic acid are mixed and concentrated, the product is a water-soluble maleate.

B. [$^{11}C$]-Labeled material: N-(methyl-$^{11}C$)-N-methyl-1,2,3,4,9,9a-hexahydro-4aH-fluoren-4a-amine is prepared as in A. by substituting $^{11}CH_2O$ for formaldehyde.

C. [$^{13}C$]-Labeled material N-(methyl-$^{13}C$)-N-methyl-1,2,3,4,9,9a-hexahydro-4aH-fluoren-4a-amine is prepared as in A. by substituting $^{13}CH_2O$ for formaldehyde.

D. [$^{14}C$]-Labeled material: N-(methyl-$^{14}C$)-N-methyl-1,2,3,4,9,9a-hexahydro-4aH-fluoren-4a-amine is prepared as in A. by substituting $^{14}CH_2O$ for formaldehyde.

EXAMPLE 3

N-Methyl-1,4,9,9a-tetrahydro-4aH-fluoren-4a-amine

A. General procedure: A solution of 5 g of methyl 1,4,9,9a-tetrahydro-4aH-fluorene-4a-carbamate in 25 ml of ether is added with stirring to 5 g of lithium aluminum hydride in 400 ml of ether at such a rate that the reaction mixture is maintained under moderate reflux. Stirring is then continued for 16 hours after which the mixture is decomposed by the successive addition of 5 ml of water, 3.75 ml of 5N sodium hydroxide solution and 17.5 ml of water. The mixture is filtered and a slight excess of hydrogen chloride in isopropyl alcohol is added to the filtrate. The precipitated product is the desired amine hydrochloride; crystallization from methanolether provides material of mp 201° to 2° C. The free base is obtained by treating an aqueous solution of the hydrochloride with sodium hydroxide and extracting with ether. A citrate is obtained by adding a solution of the free base in methanol and concentrating the mixture.

B. Deuterium-labeled material: N-(Methyl-d$_3$)1,4,9,9a-tetrahydro-4aH-fluoren-4a-amine is prepared as in A. by substituting lithium aluminum deuteride for lithium aluminum hydride.

C. Tritium-labeled material: N-(Methyl-t$_3$)1,4,9,9a-tetrahydro-4aH-fluoren-4a-amine is prepared as in A. by substituting lithium aluminum tritide for lithium aluminum hydride.

Similarly, 7 g methyl 1,2,3,4,9,9a-hexahydro-4aH-fluorene-4a-carbamate provides N-methyl-1,2,3,4,9,9a-hexahydro-4aH-fluoren-4a-amine hydrochloride of mp 202° to 3° C.

EXAMPLE 4

N-Ethyl-N-methyl-6,7,8,9-tetrahydro-9a(5aH)dibenzofuranamine

A. General procedure: A reaction mixture prepared from 8.5 g of N-methyl-6,7,8,9-tetrahydro9a(5aH)-dibenzofuranamine, 50 ml of methylene dichloride and 4.8 g of acetic anhydride is allowed to stand at room temperature for 18 hours. The mixture is washed with one equivalent of 3N hydrochloric acid, then with dilute sodium bicarbonate solution until slightly basic. The dried methylene chloride phase is evaporated to yield a residue of N-acetyl-N-methyl-6,7,8,9-tetrahydro-ga(5aH)-dibenzofuranamine. A solution of this residue in 30 ml of anhydrous ether is gradually added to a stirred solution of 5 g of lithium aluminum hydride in 400 ml of anhydrous ether. The mixture is stirred for 18 hours and then decomposed by the successive addition of 5 ml of water, 3.75 ml of 20% sodium hydroxide solution, and 7.5 ml water. The mixture is filtered and a slight excess of hydrogen chloride in isopropyl alcohol is added to the filtrate. The precipitated N-ethyl-N-methyl-6,7,8,9-tetrahydro-9a(5aH)-dibenzofuranamine hydrochloride is recrystallized from a mixture of methanol and ether, thereby yielding a material with mp about 138° to 139° C. The free base is obtained by treating an aqueous solution of the hydrochloride with sodium hydroxide and extracting with ether. A citrate is obtained by adding a solution of citric acid in methanol to a solution of the free base in methanol and concentrating.

B. Deuterium-labeled material N-(Ethyl-1,1-$d_2$)N-methyl-6,7,8,9-tetrahydro-9a(5aH)-dibenzofuranamine is prepared as in A. by substituting lithium aluminum deuteride for lithium aluminum hydride.

C. Tritium-labeled material: N-(Ethyl-1,1-$t_2$)N-methyl-6,7,8,9-tetrahydro-9a(5aH)-dibenzofuranamine is prepared as in A. by substituting lithium aluminum tritide for lithium aluminum hydride.

The corresponding dibenzothiophenamine is prepared in a similar fashion.

Double-labeled material may also be prepared using a combination of methods.

EXAMPLE 5

N-(3,3,3-Trifluoropropyl)-1,2,3,4,9,9a-hexahydro-4aH-fluoren-4a-amine

A. General procedure: To 10 mg of 1,2,3,4,9,9a-hexahydro-4aH-fluoren-4a-amine dissolved in 10 ml of acetonitrile is added with stirring 1 mg of 3-iodo-1,1,1-trifluoropropane in 1 ml acetonitrile. Purification is accomplished by chromatography, affording the desired trifluoropropyl amine. Aternatively, hydrogen, chlorine, or bromine may replace one or more of the fluorines, and nitromethane or ethyl acetate, for example, may substitute for acetonitrile. Iodine may also be replaced, for example, with mesylate or triflate moieties.

B. Replacing 3-iodo-1,1,1-trifluoropropane in A. with 3-iodo-(1,1,1-trifluoro-$^{18}F_3$)-propane affords N-(3,3,3-trifluoropropyl-$^{18}F_3$)-1,2,3,4,9,9a-hexahydro4aH-fluoren-4a-amine.

I claim:
1. A compound selected from the group consisting of:
   1,2,3,4,9,9a-hexahydro-(N-methyl-$^{11}C$)-4aH-fluoren-4a-amine,
   1,4,9,9a-tetrahydro-(N-methyl-$^{11}C$)-4a-fluoren-4a-amine,
   1,4,9,9a-tetrahydro-(N-ethyl-(2-$^{11}C$)-4a-fluoren-4a-amine, and
   1,4,9,9a-tetrahydro-(N-(3,3,3-trifluoropropyl-$^{18}F_3$))-4aHfluoren-4a-amine.

2. A method of diagnosing a central nervous system disorder in a patient which comprises administering to said patient to detectable amount of a compound according to claim 1 followed by comparative analysis using an isotopically-sensitive imaging scanner.

3. A method according to claim 2 wherein 1 femtogram per kilogram to 1 gram per kilogram body weight of a compound or a pharmaceutically acceptable salt thereof is used.

4. A method according to claim 3 wherein a compound is administered intravenously.

* * * * *

UNITED STATES PATENT AND TRADEMARK OFFICE
CERTIFICATE OF CORRECTION

PATENT NO. : 4,960,815
DATED : October 2, 1990
INVENTOR(S) : Walter H. Moos

It is certified that error appears in the above-identified patent and that said Letters Patent is hereby corrected as shown below:

Column 16, line 23: should read as follows:

1,4,9,9a-tetrahydro-(N-methyl-$^{11}$C)-4aH-fluoren-4a-amine,

Column 16, line 25: should read as follows:

1,4,9,9a-tetrahydro-(N-ethyl-(2-$^{11}$C))-4aH-fluoren-4a-amine, and

Column 16, line 27: should read as follows:

1,4,9,9a-tetrahydro-(N-(3,3,3-trifluoropropyl-$^{18}$F$_3$))-4aH-fluoren-4a-amine.

Signed and Sealed this

Fifth Day of May, 1992

Attest:

DOUGLAS B. COMER

*Attesting Officer*   *Acting Commissioner of Patents and Trademarks*